United States Patent
Bragin et al.

(10) Patent No.: US 9,763,975 B1
(45) Date of Patent: Sep. 19, 2017

(54) RHEOLOGICAL TREATMENT OF BRAIN ISCHEMIA BY DRAG REDUCING POLYMERS

(71) Applicants: Denis Bragin, Albuquerque, NM (US); Edwin Nemoto, Albuquerque, NM (US); Marina V. Kameneva, Pittsburgh, PA (US)

(72) Inventors: Denis Bragin, Albuquerque, NM (US); Edwin Nemoto, Albuquerque, NM (US); Marina V. Kameneva, Pittsburgh, PA (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/789,669

(22) Filed: Jul. 1, 2015

Related U.S. Application Data

(60) Provisional application No. 62/019,504, filed on Jul. 1, 2014.

(51) Int. Cl.
*A61K 31/765* (2006.01)

(52) U.S. Cl.
CPC ............................... *A61K 31/765* (2013.01)

(58) Field of Classification Search
None
See application file for complete search history.

(56) References Cited

U.S. PATENT DOCUMENTS

2010/0098768 A1* 4/2010 Andreescu ........... A61K 9/5094
424/489

OTHER PUBLICATIONS

Konorova et al., "Influence of Plasma DNA on Acid—Base Balance, Blood Gas Measurement, and Oxygen Transport in Health and Stroke" Ann. N.Y. Acad. Sci. 1137: 278-282 (2008).
Kameneva et al., "Blood soluble drag-reducing polymers prevent lethality from hemorrhagic shock in acute animal experiments" Biorheology 41 (2004) pp. 53-64.

* cited by examiner

*Primary Examiner* — Samantha Shterengarts
(74) *Attorney, Agent, or Firm* — Gonzales Patent Services; Ellen M. Gonzales

(57) ABSTRACT

Methods and compositions for the treatment of acute or chronic cerebral ischemia by delivery of linear, blood soluble, non-toxic macromolecules.

15 Claims, 12 Drawing Sheets

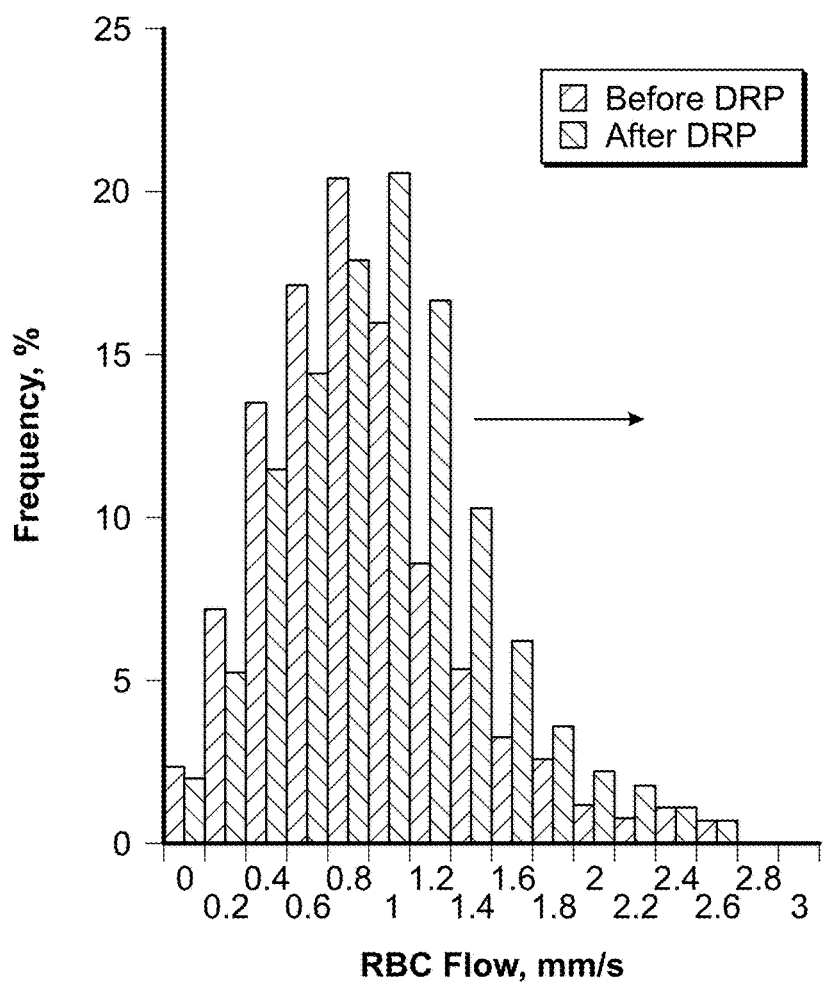
FIG. 7
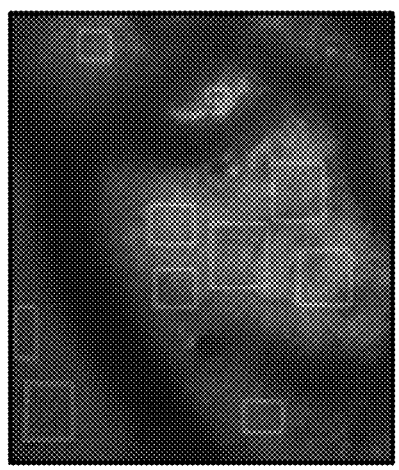 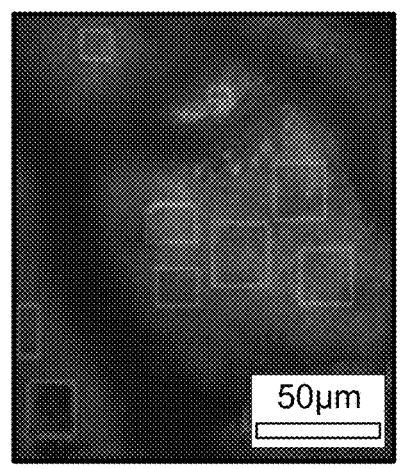
FIG. 8　　　　　　　FIG. 9

RHEOLOGICAL TREATMENT OF BRAIN ISCHEMIA BY DRAG REDUCING POLYMERS

CROSS-REFERENCE TO RELATED APPLICATIONS

The following application claims benefit of U.S. Provisional Application No. 62/019,504, filed Jul. 1, 2014, which is hereby incorporated by reference in its entirety.

BACKGROUND

Compromised cerebral perfusion, also known as brain ischemia after various cerebral insults such as cerebrovascular accidents (CVA) including ischemic or hemorrhagic stroke, subarachnoid hemorrhage, subdural hemorrhage, intracerebral hemorrhage or chronic conditions, and traumatic brain injury (TBI) invariably leads to neuronal death in a restricted area or "core" due to lack of oxygen and nutrient delivery. The brain is especially vulnerable to oxygen and nutrient deprivation because of its high rate of metabolism consuming 25% of whole body oxygen uptake while representing only approximately 3-4% of total body weight while lacking significant oxygen or glucose stores. Brain tissue oxygen is depleted within 6 seconds and the EEG is isoelectric with 25 seconds of complete circulatory arrest. Brain ischemia can be acute as in acute ischemic stroke or chronic (i.e., long-lasting) as in vascular dementia. Acute ischemia is a neurologic emergency because irreversible damage to tissues can occur within several minutes whereas chronic ischemia may occur in slow developing ischemic diseases as in vascular dementia, Alzheimer's Disease or in sickle cell disease.

Stroke and traumatic brain injury are the most frequent cerebral insults complicated by acute ischemia, and are serious global health problems causing long-term disability. Each year, about 800,000 people suffer new or recurrent stroke, which kills 130,000 of them and causes loss to the United States economy of $71.55 billion [1, 2]. Annually, 1.7 million people suffer TBI, 52,000 die and 275,000 are hospitalized for long periods of time due to secondary injury complications [3, 4]. The annual economic burden for TBI in the United States is approximately $60 billion. More than 1.1 million Americans are living with permanent functional disabilities resulting from stroke and 5.3 million from TBI representing more than 2% of the US population. Currently, there are no neuroprotective strategies proven effective in improving outcome after CVA or TBI despite the many therapies that have been found effective in animals only to fail in clinical trials. In the treatment of acute ischemic stroke, thrombolysis with tissue plasminogen activator (tPA) for thrombolysis of the clot is the only FDA approved treatment. However, only 5-7% of patients qualify for thrombolytic therapy due to the increased with time after stroke risk of hemorrhagic transformation [5, 6] and only about 30% of those treated recanalize. Notably, none of the neuroprotective therapies tested thus far have sought to focus on hemorheological restoration or improvement of impaired microvascular perfusion.

Traumatic brain injury (TBI) with post-traumatic high intracranial pressure (ICP) [3,4], another condition leading to brain ischemia, also known as intracranial hypertension, is fatal by arresting cerebral blood flow (CBF) to the entire brain even in cases of focal injury. It leads to cerebral edema and expansion of the blood volume within the brain, tissue compression, shift in brain structures, and brain herniation restricting blood supply to the entire brain leading to brain death.

Other incidents and conditions associated with acute or chronic brain ischemia are: global cerebral ischemia caused by cardiac arrest, heart failure or hemorrhagic shock; chronic intracranial hypertension, including idiopathic intracranial hypertension, hydrocephalus and pseudo tumor cerebri; mild cognitive impairment, including vascular dementia and Alzheimer's disease; systemic lupus erythromatosus; multiple sclerosis; Moyamoya disease; transient ischemic attacks; hypertensive encephalopathy and ruptured aneurysm.

The treatments available for ischemia are limited and require novel solutions which involve looking at the problem and possible solutions from a new perspective. Numerous neuroprotective treatments found effective in animals, have failed to translate clinically [7, 8].

As a specific example, Alzheimer's disease (AD) which presently affects more than 5 million Americans and projected to increase to 16 million by 2050 [1], is a consequence of complex interactions of age-related neurodegeneration and vascular-associated pathologies. The quantitative neuropathologic criteria for AD diagnostics as well as the main target for treatment options are the degree of deposition of amyloid plaques and Tau protein neurofibrillary tangles [2]. However, treatments aimed to prevent or remove amyloid plaques have not succeeded in preventing or reducing dementia [3, 4].

Similarly, to date, the only FDA-approved treatment for ischemic stroke, tissue plasminogen activator (tPA), is used only in 5% of these patients because the therapeutic window is prohibitively short (3 hours after the event) due to a 10-fold increased incidence of intracranial hemorrhage with 50% mortality [5, 6]. In recent years, studies showed the importance of collateral flow which may provide an alternative route for blood to reach the ischemic tissue and partially maintain oxygen support in ischemic stroke [29]. Extensive anastomotic connections between the anterior and middle cerebral arteries have been shown after occlusion [30, 31] and persisted for 24 hours [30]. It is suggested that enhancement of collateral blood flow to ischemic territories may benefit stroke patients. Studies showed that collateral treatment such as i.v. injection of high dose of albumin blood pressure augmentation [32] and partial occlusion of the aorta [33, 34] may reduce infarction and improve recovery after stroke, however, these methods have various complications [35], like volume expansion, hemodilution and reduced viscosity which improved microvascular perfusion in rodents but worsened outcome in patients due to pulmonary edema (albumin).

Therefore, new, effective approaches to treat, ameliorate or prevent brain ischemia caused by various etiologies are still urgently needed.

SUMMARY

The present disclosure provides methods and compositions for the treatment of acute or chronic cerebral ischemia by targeting the very basis of ischemia by improving the rheology of blood flow through arteries and capillaries and as such would be relevant in the treatment, amelioration, or prevention of acute and chronic ischemic conditions of various etiologies. According to a first embodiment, the present disclosure provides linear, blood soluble, non-toxic macromolecules, referred to herein as drag-reducing polymers (DRPs) for the treatment, amelioration or prevention of brain (and other organs) ischemia and other conditions or injuries causing or potentially leading to ischemic injury. According to a second embodiment, the present disclosure provides a method for treating, ameliorating or preventing brain (and other organs) ischemia of varying etiologies by the administration of DRP to a subject.

BRIEF DESCRIPTION OF THE DRAWINGS

FIG. 7 is a frequency histogram showing flow velocity increase after DRP injection.

FIG. 8 shows cortical NADH fluorescence at baseline.

FIG. 9 shows cortical NADH fluorescence after DRP injection.

FIG. 20A is the baseline flow.

FIG. 20B is the MVS flow after ICP increase.

FIG. 20C is flow after DRP treatment.

FIG. 21A is a representative T1 Magnetic Resonance image of rat brain before TBI.

FIG. 21B is a representative T1 Magnetic Resonance image of rat brain 2 hours after TBI showing tissue damage in the left hemisphere.

DETAILED DESCRIPTION

According to an embodiment the present disclosure provides novel methods and compositions for treating, ameliorating or preventing brain (and other organs) ischemia of various etiologies. According to various embodiments, brain ischemia, caused by different conditions, accidents or injuries in a subject are treated, ameliorated or prevented by intravenous (or through any other route) delivery of one or more polymers that enhance blood flow by modulation of hemodynamics, thereby improving oxygen and nutrients delivery to tissue.

Figure 1:
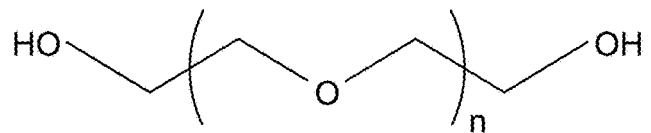
FIG. 1 is the chemical formula of polyethylene oxide.

In general, polymers suitable for use with the presently described methods include linear, blood soluble non-toxic macromolecules with a molecular weight over $10^6$ Daltons, which are commonly referred to as drag-reducing polymers (DRPs.) Suitable DRPs exist as both naturally-occurring and synthetic polymers. Examples of naturally occurring DRPs include linear, blood soluble non-toxic polysaccharides and polypeptides derived from plants such as okra, aloe vera and others, algae, gums, polypeptides and polysaccharides derived from bacteria, polymers derived from fish slimes, sea-water and fresh-water biological growths, ovomucin of egg-whites, biopolymers derived from human or animal blood, blood plasma and blood cells. Specific examples include high molecular weight polyethylene oxide (the chemical formula of which is shown in FIG. 1) and hyaluronic acid. Non-natural synthetic polymers may be selected from of water soluble synthetic high-molecular weight polymers such as high molecular weight polyethylene oxides, polyacrylamides, etc. As non-limiting examples, products with the following tradenames and available from the following companies may be useful: Polyethylene oxides (Polyox water soluble resins WSR-301, 309, N60K, N-750 and others, Union Carbide Co., USA) polyacrylamides (Praestol 2515TR, 2540TR and others, Stockhausen, Inc., Sweden), Carboxymethyl cellulose (Gum Technology Co.), gums such as Gum Guar (Sigma Chemical Co.), Tragacanth (Gum Technology Co.), Gum Karaya (Sigma Chemical Co.), Gum Xanthan (Sigma Chemical Co.).

The precise mechanisms of action of DRPs are unknown, but they are thought to reduce pressure loss in small arteries and arterioles by diminishing flow separations and vortices at vessel bifurcations and thereby, increasing pre-capillary pressure, increasing the density of perfused capillaries and elimination of capillary stasis due to ischemia or other pathological conditions [9-14]. The net effect is improved microcirculation and increased red blood cell (RBC) traffic in microvessels [12, 13, 15]. DRP also reduced the thickness of the near-wall cell free layer that normally exists in vessels with <300 μm diam. The alignment and stretching of the polymer molecules along the flow paths may diminish RBC rotation, which is an important contributor to the formation of the near-wall plasma layer [11, 12]. A decrease of the cell-free layer also reduces plasma skimming at vessel bifurcations resulting in more RBC entering distal branches which increases the number of RBC in capillaries [11, 12] and decreases near-wall platelet concentration [14]. Nanomolar concentrations of intravenous DRPs have been shown to improve hemodynamics and survival in animal models of the ischemic myocardium [16-18], ischemic limb [19] and hemorrhagic shock [11, 20][30, 32][26][33][31, 34]. Despite the promising results in other systems there are no studies on the DRP in the brain. In the only observation, published in Russian, Gannushkina et al. reported that DRP qualitatively improved perfusion in rabbits after global ischemia [21]. As demonstrated in the Examples section below, we have demonstrated in a healthy rat brain that DRP increases blood flow rate in arterioles and enhances perfusion and oxygenation [22]. We also showed that DRPs restore perfusion in collapsed capillaries, reduces non-nutritive microvascular shunt flow and tissue hypoxia in hypertensive and traumatized brain [23]. Modulation of the cerebral circulation by DRPs also overcame the effects of blood flow stasis in the ischemic penumbra after acute ischemic stroke as we reported recently [24]. In both TBI and pMCAO models, hemorheologic effects of intravenous DRPs translated into long-term improvement in clinically relevant anatomical and neurologic outcome.

According to our studies, we believe the impact of delivering DRP to subjects who are suffering from or who have suffered from an ischemic event extends beyond simply increasing blood flow, which, aside from improving the delivery of oxygen and nutrients to the brain, reverses low vascular wall shear stress, which includes endothelium mediated pro-inflammatory processes and apoptosis. The vascular wall is highly sensitive to the hydrodynamic forces exerted on the endothelium by flowing blood, which affects the endothelial phenotype by regulating the activity of flow sensitive proteins [25]. DRPs were previously shown to increase vessel wall shear stresses in microcirculation by modulation of the blood cell traffic [9]. Vascular wall shear stresses maintain levels of nitric oxide release and vasodilation by activation of eNOS at the apical membrane of endothelial cells. Endothelial wall shear stress controls apoptosis and regulates lymphocyte adhesion to the vessel wall all of which would be normalized and stabilized by DRPs, leading to improvement of compromised flow in the ischemic penumbra [26-28].

DRPs, by enhancement of systemic blood flow, increase collateral flow and, thus, can be considered as novel "collateral therapeutics" which overcome the effects of blood flow stasis in the penumbra after ischemic stroke. Accordingly, the present disclosure provides for the delivery of one or more types of DRPs to a subject before, during or after an ischemic event. As non-limiting examples, DRPs could be administered, as a preventative measure, to a subject believed to be at risk of vascular dementia, during an ischemic event in an attempt to reduce or eliminate damage caused by the event, and as an ameliorative measure for a patient who has suffered a stroke after the time window for tPA or other known therapies has ended. According to various embodiments, delivery of the DRPs can be in conjunction with or in lieu of other therapies.

According to various embodiments, the present disclosure further provides the use of DRPs in all acute and chronic brain (and other organ) ischemia caused by various etiologies in the acute as well as the recovery phase days after the initial insult, which could make a tremendous impact on the prevention of secondary brain damage as well as amelioration of the effects of the original event.

According to some embodiments, the polymers described herein may be modified to increase their efficacy as biologicals. For example, the polymers could be modified to increase water solubility and/or stability.

According to various embodiments, the DRPs are delivered in nanomolar concentrations. According to various embodiments, the DRPs are delivered in such a way that a desired final blood concentration is achieved. According to some embodiments the desired final blood concentration is between 0.1 and 5 (μg/ml). According to a more specific embodiment, the final blood concentration is 2 ppm. The DRP may be formulated as a sterile solution in an appropriate pharmaceutical buffer or carrier. Examples of suitable buffers include, but are not limited to, normal saline, phosphate buffer saline (PBS) or any other physiological saline.

Delivery can be given intravenously as a single dose, multiple separate doses, or via a constant delivery mechanism (i.e. an infusion pump). According to various embodiments, the dose(s) may be delivered via a single injection, repetitive injection, or continuous dripping or infusion. According to a further embodiment the present disclosure provides a constant delivery mechanism designed to maintain a desired DRP concentration (e.g. between 0.1 and 5 ppm) in the subject's blood for an extended or even indefinite period of time. According to various embodiments, this extended period of time could be multiple hours, days, weeks, months, or even years.

According to some embodiments, this constant delivery mechanism could be used in subjects suffering from chronic conditions such as Alzheimer's, Parkinson's or other type of vascular dementia. Alternatively or additionally such a device could be configured to monitor blood flow velocity (via, for example, an integrated Doppler) and/or DRP concentration and deliver an appropriate constant or variable dosage of DRP to maintain a desired blood flow velocity and/or DRP concentration. In this configuration it will be understood that the "constant delivery mechanism" may not, in fact, deliver a constant dosage of DRP to the target subject, but rather would be configured to deliver an appropriate dosage when and as needed. It should be understood that other, non-intravenous delivery options may also be used oral, rectal, and transcutaneous methods.

Examples of conditions and diseases that may receive benefit from the presently described methods include, but are not necessarily limited to: events/conditions/diseases affecting the brain including cerebrovascular accidents of various etiologies, including thrombosis, embolism, systemic hypoperfusion and venous thrombosis; traumatic brain injuries of various etiology, including injuries with secondary complications such as hemorrhagic shock and high intracranial pressure; global cerebral ischemia caused by cardiac arrest, heart failure or hemorrhagic shock; intracranial hypertension, leading to chronic ischemia, including idiopathic intracranial hypertension, hydrocephalus and pseudo tumor cerebri; mild cognitive impairment; vascular dementia; Alzheimer's disease; systemic lupus erythromatosus; multiple sclerosis; Moyamoya disease; transient ischemic attacks; hypertensive encephalopathy; to reduce aneurism formation or to prevent it's rupture by reducing turbulent flow; and other types of brain ischemia and conditions potentially leading to brain ischemia not listed here. Moreover, additional organ systems or pathologies that might derive benefit include: sickle cell anemia; compartment syndrome; peripheral vascular disease; and diabetic neuropathy.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

References: All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

1. Minino, A. M., et al., *Deaths: final data for* 2008. Natl Vital Stat Rep, 2011. 59(10): p. 1-126.
2. http://www.cdc.gov/stroke/facts.htm.
3. *Traumatic Brain Injury in the US. Center for Disease Control.* 2010; Available from: http://braininjury.blogs.com/braininjury/2010/03/cdc-releases-latest-statistics-on-traumatic-brain-injury.html.
4. Langlois, J. A., W. Rutland-Brown, and M. M. Wald, *The epidemiology and impact of traumatic brain injury: a brief overview.* J Head Trauma Rehabil, 2006. 21(5): p. 375-8.
5. Adams, H., et al., *Guidelines for the early management of patients with ischemic stroke:* 2005 *guidelines update a scientific statement from the Stroke Council of the American Heart Association/American Stroke Association.* Stroke, 2005. 36(4): p. 916-23.
6. Adams, H. P., Jr., et al., *Guidelines for the early management of adults with ischemic stroke: a guideline from the American Heart Association/American Stroke Association Stroke Council, Clinical Cardiology Council, Cardiovascular Radiology and Intervention Council, and the Atherosclerotic Peripheral Vascular Disease and Quality of Care Outcomes in Research Interdisciplinary Working Groups: the American Academy of Neurology affirms the value of this guideline as an educational tool for neurologists.* Stroke, 2007. 38(5): p. 1655-711.
7. Albers, G. W., et al., *Stroke Treatment Academic Industry Roundtable (STAIR) recommendations for maximizing the use of intravenous thrombolytics and expanding treatment options with intra-arterial and neuroprotective therapies.* Stroke, 2011. 42(9): p. 2645-50.
8. Jain, K. K., *Neuroprotection in cerebrovascular disease.* Expert Opin Investig Drugs, 2000. 9(4): p. 695-711.
9. Kameneva, M. V., *Microrheological effects of drag-reducing polymers in vitro and in vivo.* International Journal of Engineering Science, 2012. 59: p. 168-183.
10. Kameneva, M. V., M. S. Poliakova, and I. A. Gvozdkova, [*The nature of the effect of polymers reducing hydrodynamic resistance on blood circulation*]. Dokl Akad Nauk SSSR, 1988. 298(5): p. 1253-6.
11. Kameneva, M. V., et al., *Blood soluble drag-reducing polymers prevent lethality from hemorrhagic shock in acute animal experiments.* Biorheology, 2004. 41(1): p. 53-64.
12. Marhefka, J. N., et al., *Drag reducing polymers improve tissue perfusion via modification of the RBC traffic in microvessels.* Biorheology, 2009. 46(4): p. 281-92.
13. Pacella, J. J., et al., *Modulation of pre-capillary arteriolar pressure with drag-reducing polymers: a novel method for enhancing microvascular perfusion.* Microcirculation, 2012. 19(7): p. 580-5.
14. Zhao, R., et al., *Drag-reducing polymers diminish near-wall concentration of platelets in microchannel blood flow.* Biorheology, 2010. 47(3-4): p. 193-203.
15. Pranevicius, M. and O. Pranevicius, *Cerebral venous steal: blood flow diversion with increased tissue pressure.* Neurosurgery, 2002. 51(5): p. 1267-73; discussion 1273-4.
16. Pacella, J. J., et al., *A novel hydrodynamic approach to the treatment of coronary artery disease.* Eur Heart J, 2006. 27(19): p. 2362-9.
17. Pacella, J. J., M. V. Kameneva, and F. S. Villanueva, *Drag reducing polymers improve coronary flow reserve through modulation of capillary resistance.* Biorheology, 2009. 46(5): p. 365-78.
18. Sakai, T., et al., *I.V. infusion of a drag-reducing polymer extracted from aloe vera prolonged survival time in a rat model of acute myocardial ischaemia.* Br J Anaesth, 2007. 98(1): p. 23-8.
19. Hu, F., et al., *Improvement of the microcirculation in the acute ischemic rat limb during intravenous infusion of drag-reducing polymers.* Biorheology, 2011. 48(3-4): p. 149-59.

20. McCloskey, C. A., et al., *Tissue hypoxia activates JNK in the liver during hemorrhagic shock*. Shock, 2004. 22(4): p. 380-6.
21. Gannushkina, I. V., et al., [*Possibility of restoring the cerebral blood flow in cerebral ischemia by injecting special polymers into the blood*]. Patol Fiziol Eksp Ter, 1982(3): p. 58-9.
22. Bragin, D. E., Thompson, S., Statom, G., Kameneva, M. V., Nemoto, E. M., *Drag-reducing polymer improves microvascular flow and tissue oxygenation in the normal and traumatized rat brain*. Journal of Neurotrauma, Abstracts from the 31st Annual National Neurotrauma Symposium, Nashville, Tenn., 2013. 30(15): p. C165.
23. Bragin, D. E., Thomson, S., Bragina, O. A., Statom, G., Kameneva, M. V., Nemoto, E. M. *Drag reducing polymer enhances microvascular perfusion in the traumatized brain with intracranial hypertension*. in Abstract book for the 15th International Symposium on Intracranial Pressure and Brain Monitoring 2013. Singapore.
24. Bragin, D. E., Peng, Z., Liu, W., Thomson, S., Statom, G., Kameneva, M. V., N, E. Memoto, *Drag-Reducing Polymer Improves Microcirculation and Outcome after Permanent Middle Cerebral Artery Occlusion in Rats* Stroke, Abstracts from the International Stroke Conference, San Diego, Calif., 2014. 45.
25. Topper, J. N. and M. A. Gimbrone, Jr., *Blood flow and vascular gene expression: fluid shear stress as a modulator of endothelial phenotype*. Mol Med Today, 1999. 5(1): p. 40-6.
26. Ji, J. Y., H. Jing, and S. L. Diamond, *Hemodynamic regulation of inflammation at the endothelial-neutrophil interface*. Ann Biomed Eng, 2008. 36(4): p. 586-95.
27. Resnick, N., et al., *Fluid shear stress and the vascular endothelium: for better and for worse*. Prog Biophys Mol Biol, 2003. 81(3): p. 177-99.
28. Yang, B. and V. Rizzo, *Shear Stress Activates eNOS at the Endothelial Apical Surface Through 1 Containing Integrins and Caveolae*. Cell Mol Bioeng, 2013. 6(3): p. 346-354.
29. Liebeskind, D. S., *Collateral therapeutics for cerebral ischemia*. Expert Rev Neurother, 2004. 4(2): p. 255-65.
30. Armitage, G. A., et al., *Laser speckle contrast imaging of collateral bloodflow during acute ischemic stroke*. J Cereb Blood Flow Metab, 2010. 30(8): p. 1432-6.
31. Wang, Z., et al., *Dynamic change of collateral flow varying with distribution of regional blood flow in acute ischemic rat cortex*. J Biomed Opt, 2012. 17(12): p. 125001.
32. Shin, H. K., et al., *Mild induced hypertension improves blood flow and oxygen metabolism in transient focal cerebral ischemia*. Stroke, 2008. 39(5): p. 1548-55.
33. Noor, R., et al., *Partial intra-aortic occlusion improves perfusion deficits and infarct size following focal cerebral ischemia*. J Neuroimaging, 2010. 20(3): p. 272-6.
34. Uflacker, R., C. Schonholz, and N. Papamitsakis, *Interim report of the SENTIS trial: cerebral perfusion augmentation via partial aortic occlusion in acute ischemic stroke*. J Cardiovasc Surg (Torino), 2008. 49(6): p. 715-21.
35. Liebeskind, D. S., *Collaterals in acute stroke: beyond the clot*. Neuroimaging Clin N Am, 2005. 15(3): p. 553-73, x.
36. Gerriets, T., et al., *Noninvasive quantification of brain edema and the space-occupying effect in rat stroke models using magnetic resonance imaging*. Stroke, 2004. 35(2): p. 566-71.
37. Lin, T. N., et al., *Effect of brain edema on infarct volume in a focal cerebral ischemia model in rats*. Stroke, 1993. 24(1): p. 117-21.
38. Butler, T. L., et al., *Neurodegeneration in the rat hippocampus and striatum after middle cerebral artery occlusion*. Brain Res, 2002. 929(2): p. 252-60.
39. Schmued, L. C. and K. J. Hopkins, *Fluoro-Jade B: a high affinity fluorescent marker for the localization of neuronal degeneration*. Brain Res, 2000. 874(2): p. 123-30.
40. Bragin, D. E., et al., *Differential changes of glutathione levels in astrocytes and neurons in ischemic brains by two-photon imaging*. J Cereb Blood Flow Metab, 2010. 30(4): p. 734-8.
41. Fujii, K., et al., *Effect of antihypertensive treatment on focal cerebral infarction*. Hypertension, 1992. 19(6 Pt 2): p. 713-6.
42. Bragin, D. E., et al., *High intracranial pressure effects on cerebral cortical microvascular flow in rats*. J Neurotrauma, 2011. 28(5): p. 775-85.
43. Bragin, D. E., Statom, G., Nemoto, E. M., *Microvascular Shunt Flow after Traumatic Brain Injury with Intracranial Hypertension in Rats*. Journal of Neurotrauma, Abstracts from The 31st Annual National Neurotrauma Symposium Aug. 4-7, 2013 Nashville, Tenn. 2012. 29: p. A-22.
44. Bragin, D. E., Statom, G., Nemoto, E. M., *ICP-induced microvascular shunt flow involved in pathophysiological responses in the injured brain*. Brain Injury, 2012. 26(4-5): p. 589.
45. Marhefka, J. N., et al., *Poly(N-vinylformamide)-A drag-reducing polymer for biomedical applications*. Biomacromolecules, 2006. 7(5): p. 1597-603.

Experimental

DRP Preparation and Administration.

Polyethylene oxide (PEO, MW~4500 kDa) was dissolved in normal saline [0.9% of Sodium Chloride in water] to 0.1% (1000 ppm) and dialyzed against saline using a 50 kD cutoff membrane. Before injection, the PEO solution was diluted in saline to 50 ppm and slow rocked for ~2 hours. Prepared solution was sterilized using a 0.22 micron filter prior to injection. The solution was infused intravenously over 5 min to a final blood concentration of 2 µg/ml (ppm). The volume (mL) to be infused was determined by: ([rat weight (grams)× 0.07]/50 ppm).

DRPs Enhanced the Arteriole Flow Profile and Increased RBC Flow Velocity in Capillaries Leading to Increased Tissue Oxygenation in the Healthy Rat Brain.

Figure 2:
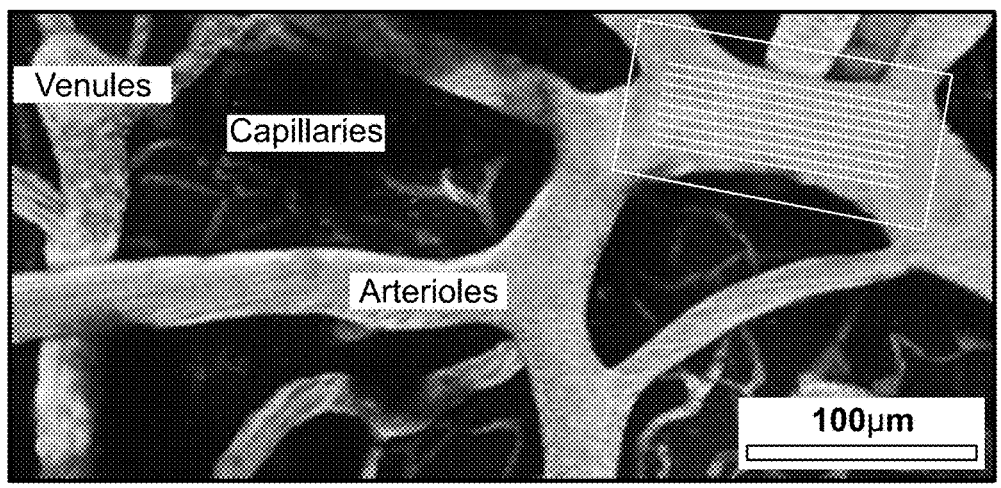
FIG. 2 is a 2PLSM micrograph of rat cortex microvasculature with line scans settings for arteriolar blood flow velocity profiles (superimposed stripes).
Figure 3:
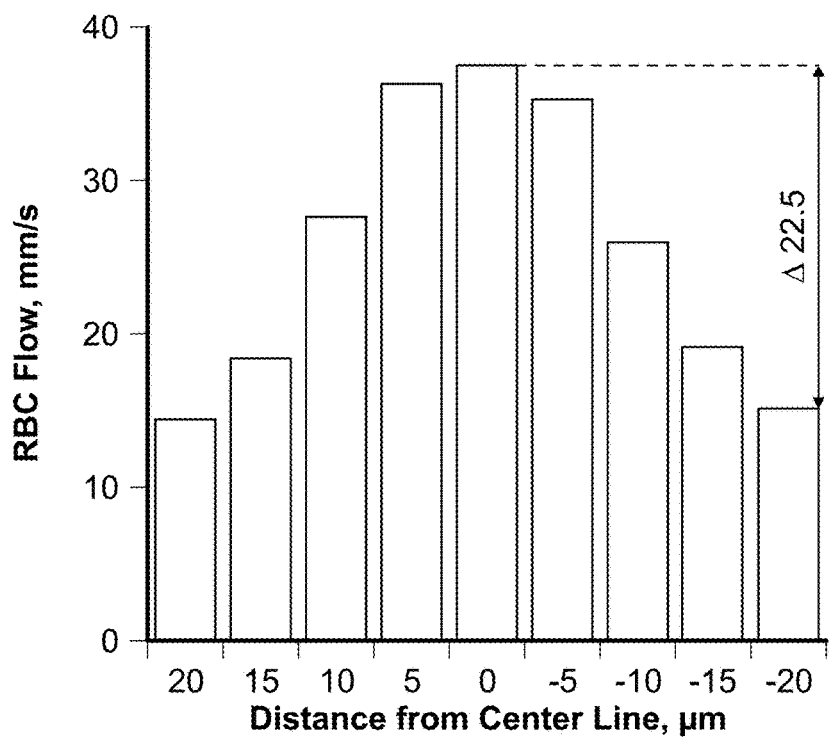
FIG. 3 shows arteriolar blood flow velocity profiles before DRP injection.
Figure 4:
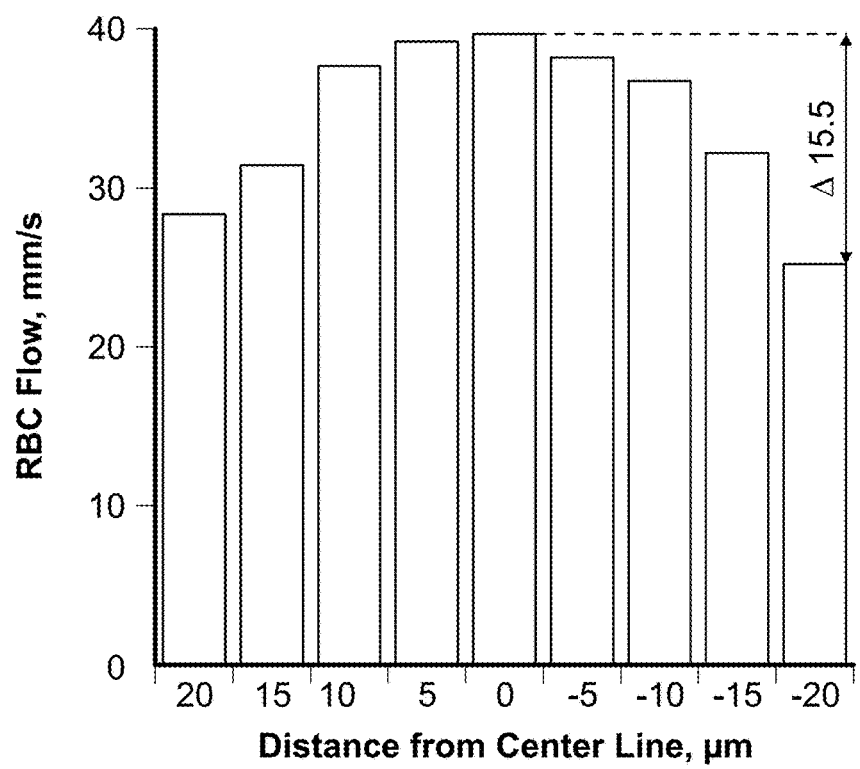
FIG. 4 shows arteriolar blood flow velocity profiles after DRP injection. Increased velocity is seen near the vessel walls (Δ, mm/s).
Figure 5:
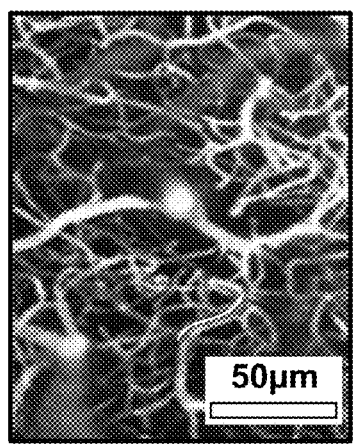
FIG. 5 shows the volume from which every individual capillary flow was recorded.
Figure 6A:
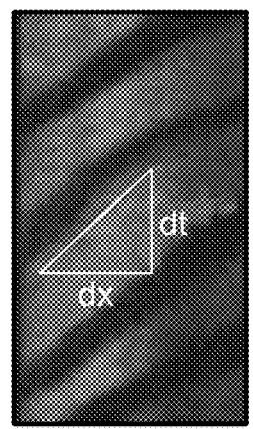
FIG. 6a is a line-scan from the capillary before DRP injection.
Figure 6B:
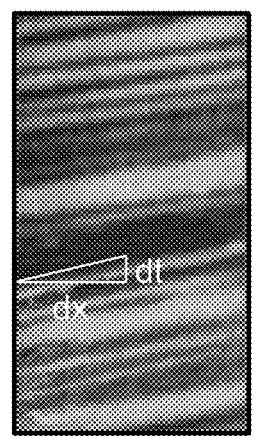
FIG. 6b is a line-scan from the capillary after DRP injection.
Figure 10:
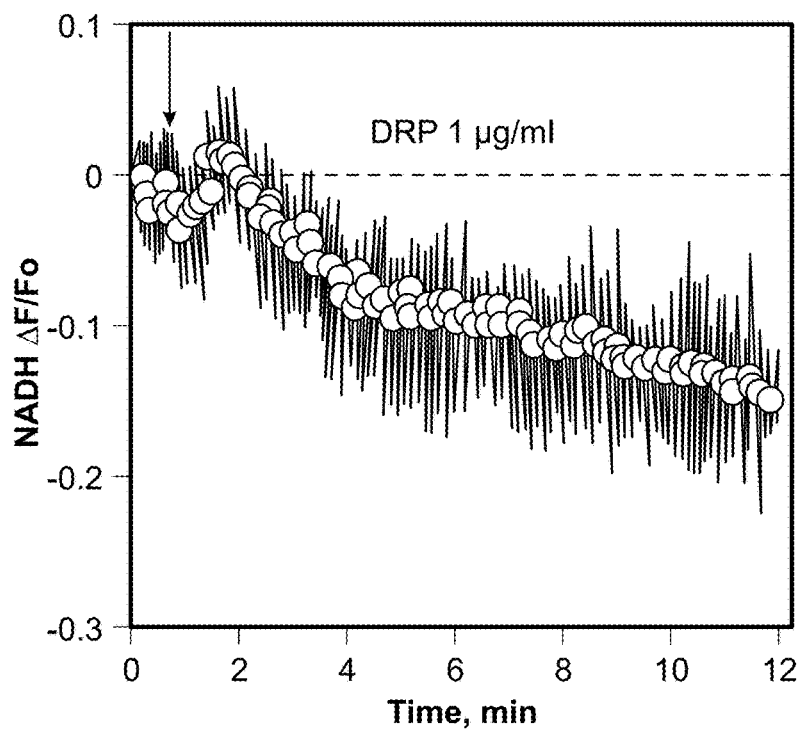
FIG. 10 is a time plot from ROIs above showing NADH decrease after DRP injection. Gray lines—ROIs values, circles—means, dashed line—base line, arrow—DRP injection. (n=10, p<0.05 for b, e and h).

Using in-vivo 2PLSM over the rat parietal cortex, we measured microvascular RBC flow velocity and NADH fluorescence. Arteriolar flow velocities obtained by line scans at different distances from midline (FIG. 2), showed flow velocity parabolic profile with a large velocity gradient from the centerline to the wall (FIG. 3). The i.v. injection of the DRPs (2 µg/ml) increased near-wall flow velocity and the flow rate in arterioles leading to an increase of blood volume perfused through the tissue presumably via reduced plasma skimming at vessel bifurcations resulting in an increase in number of RBCs entering capillaries (FIG. 4). The increased blood volume in arterioles after DRPs injection resulted in the enhanced capillary perfusion as it shown by increased RBC flow velocities by 7.2±1.4% (FIGS. 5-7). Enhanced capillary perfusion increased tissue oxygenation as reflected by a reduction in NADH autofluorescence by 7.9±2.4% (FIGS. 8-10). All changes were significantly different from a baseline (P<0.05 for all variables), and persisted for 4 hours monitored. In the control group of animals, where the same volumes of saline were injected instead of DRPs, these variables were unchanged during four hours monitored.

DRP Injection Restored Microvascular Blood Flow and Reduced Tissue Hypoxia after Acute Focal Brain Ischemia.

Figure 11:
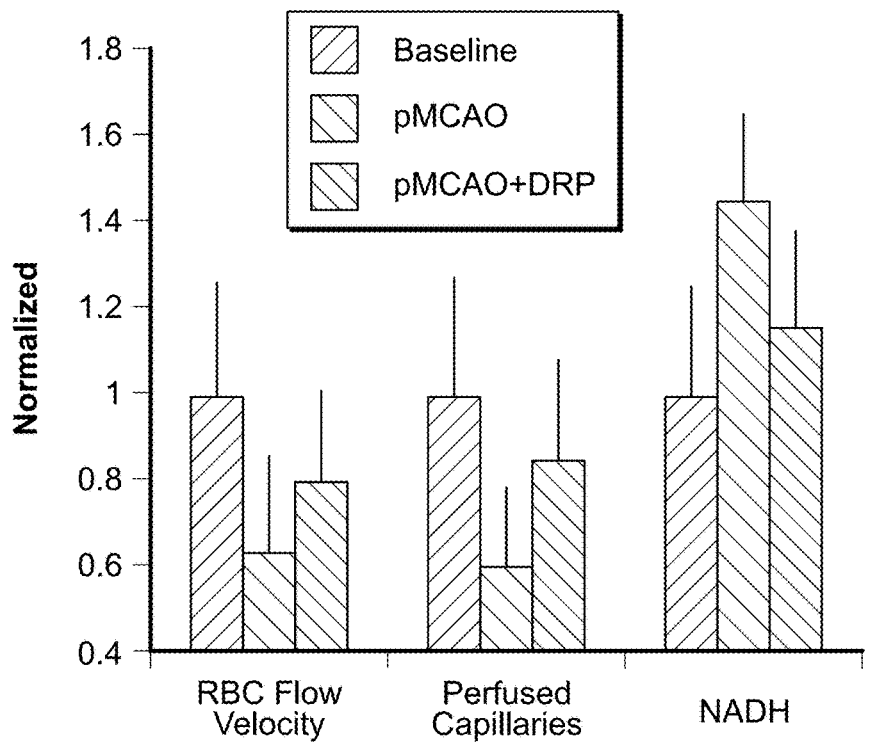
FIG. 11 is a graph showing the acute effects of DRPs on rat permanent middle cerebral artery occlusion (pMCAO). Permanent MCAO causes reduction of microvascular RBC flow velocity, capillary stasis and tissue hypoxia (as reflected by NADH increase). DRPs improve cerebral flow, restore perfusion in collapsed capillaries and attenuate tissue hypoxia (NADH). Data normalized to baseline, Mean±SEM, n=5.
Figure 12:
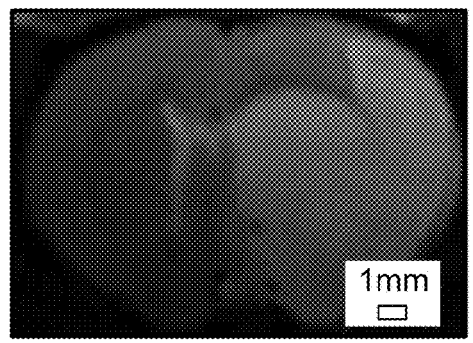
FIG. 12 is a T2 MRI showing an ischemic lesion.
Figure 13:
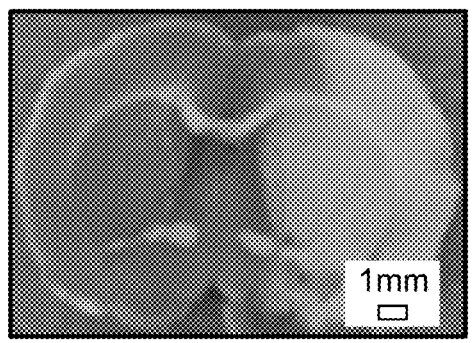
FIG. 13 is a TTC-stained brain slice showing the infarcted tissue.
Figure 14:
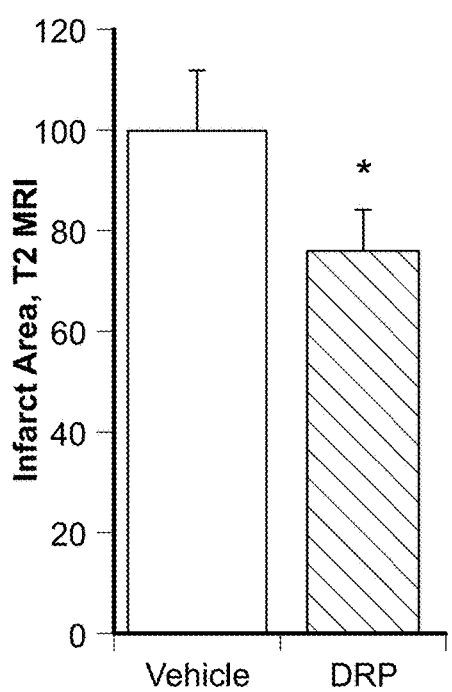
FIG. 14 is a bar graph demonstrating that DRPs treatment decreases ischemic lesion at 24 hours after pMCAO as calculated from for 2T MRI (n=4)
Figure 15:
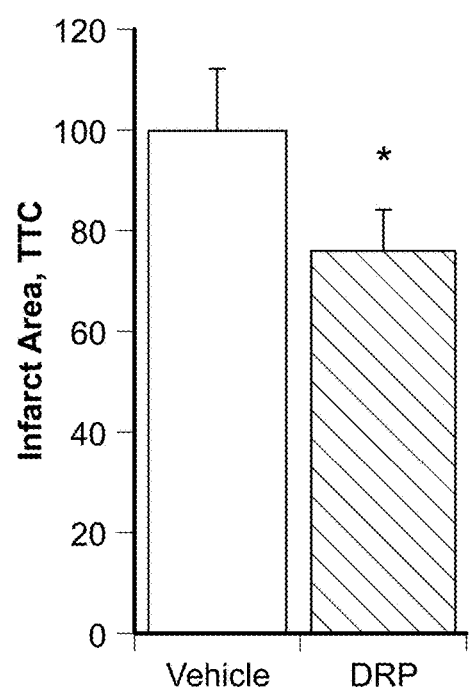
FIG. 15 is a bar graph demonstrating that DRPs treatment decreases ischemic lesion at 24 hours after pMCAO as calculated from TTC staining (n=4).

The rat suture permanent middle cerebral artery occlusion (MCAO) model of acute focal brain ischemia was used. DRPs were injected i.v. 90 minutes after pMCAO. Controls were injected with an equal volume of saline. Using in vivo 2-photon laser scanning microscopy over the parietal cortex, we studied the acute effects of DRPs on microvascular blood flow velocity and tissue oxygenation (NADH) during 5 hours after stroke onset. After baseline imaging, pMCAO was induced; imaging repeated; DRPs or saline injected and followed by imaging. pMCAO resulted in a progressive capillary stasis and compromised microvascular flow leading to tissue hypoxia in the penumbra of the parietal cortex during 5 hours monitored. DRPs partially restored blood flow in capillaries, enhanced microvascular flow velocity (21±6.7%, Mean±SEM, p<0.05, n=5) and reduced the progression of ischemia by 14±4.6 and 18±6.5% (p<0.05) compared to saline injected animals (FIG. 11).

DRPs-Related Improvement of Microvascular Flow and Tissue Oxygenation LED to Improved Clinically Relevant Outcome:

DRPs decreased infarct size at 24 hours after pMCAO by 29±12.4% and 24±8.1%, as evaluated by in-vivo T2-weighted Magnetic Resonance Imaging (MRI) and post-mortem triphenyltetrazolium chloride (TTC) staining, respectively, compared to saline treated rats (FIGS. 12-15 p<0.05, n=4). Infarction volumes were calculated with DRPs correction for edema swelling by comparison with the contralateral hemisphere [36, 37].

Figure 16:
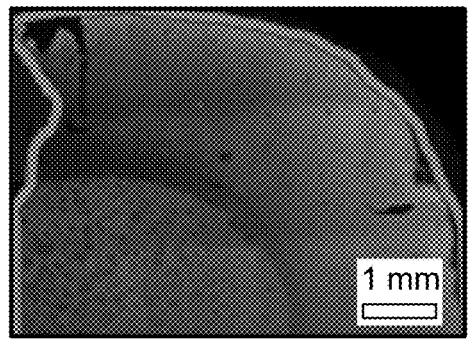
FIG. 16 shows Fluoro-Jade staining for saline treated rats at 48 hours after pMCAO. superimposed line—neurodegeneration area.
Figure 17:
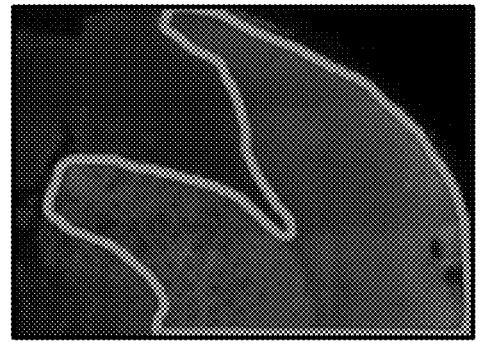
FIG. 17 shows Fluoro-Jade staining for DRP treated rats at 48 hours after pMCAO. superimposed line—neurodegeneration area.
Figure 18:
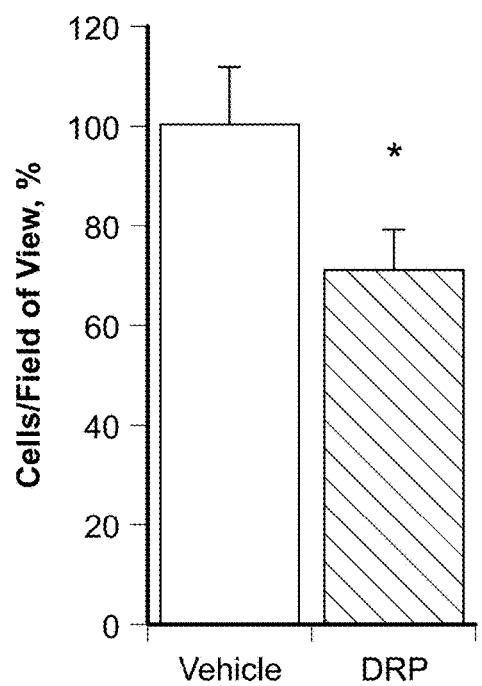
FIG. 18 is a Bar graph showing reduced neurodegeneration in DRP treated animals (n=4).

DRPs reduced neuronal degeneration as shown by Fluoro-Jade B stain [38, 39] at 48 hours after pMCAO. In saline-treated rats neurodegeneration involved nearly the entire cortex and striatum (FIG. 16); and was smaller in DRP treated rats (FIG. 17). Quantification revealed that DRPs decreased the number of degenerating neurons by 28±10.3% (FIG. 18, p<0.05, n=4).

Figure 19:
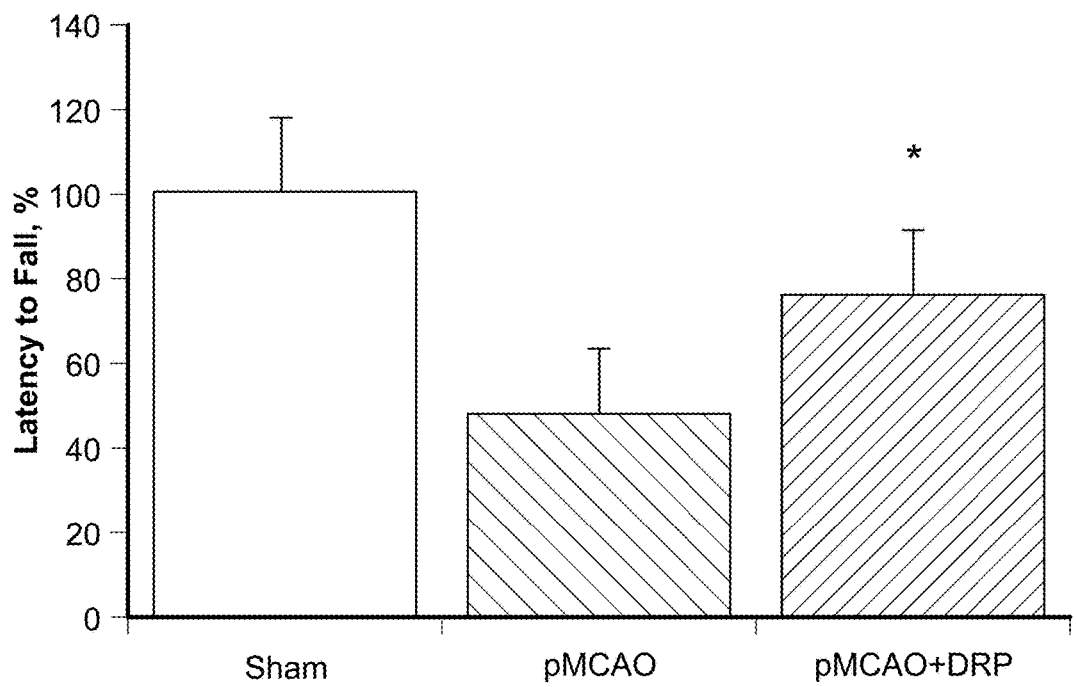
FIG. 19 is a bar graph showing the results of a rotarod test one week after pMCAO demonstrating better coordination and motor performance in DRP treated animals (n=5) compared to saline treated (n=5). Data are % of normal animals.
Figure 20A:
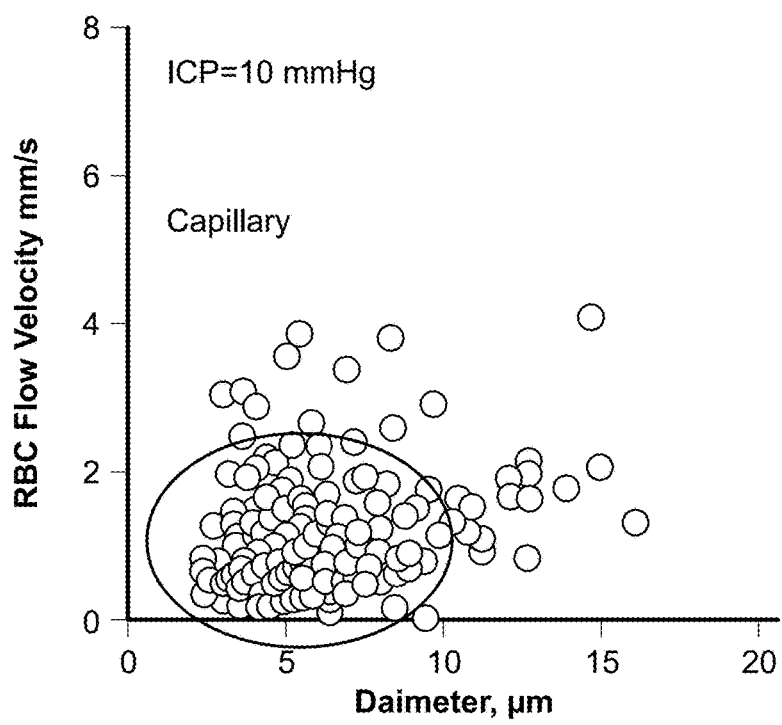
FIGS. 20A-20C are scatter plots of red blood cells (RBC) flow velocity versus vessel diameter showing stagnation of capillary flow and appearance of non-nutritive microvascular shunt (MVS) flow after ICP increase (20B) compared to baseline 20(A). DRP treatment partially restored capillary flow and reduced MVS flow (20C). light grey outline—capillary flow, dark grey outline—MVS flow.
Figure 20B:
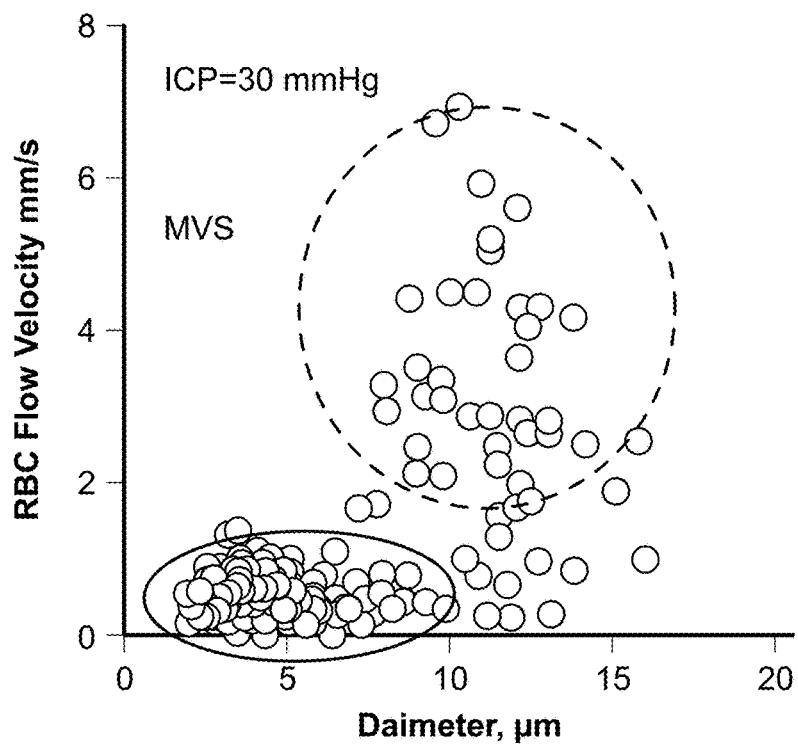
Figure 20C:
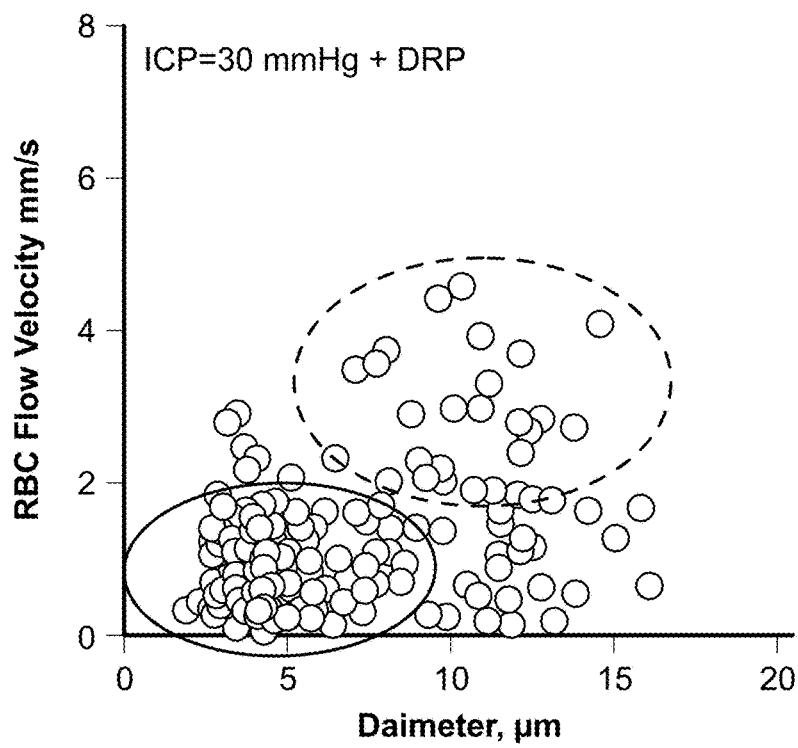
Figure 20D:
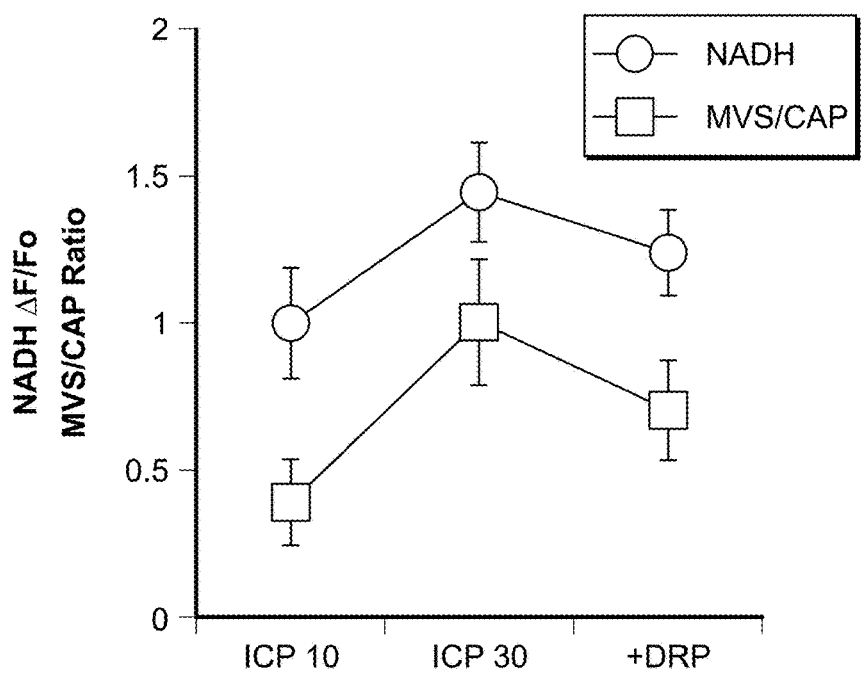
FIG. 20D is a graph showing that DRP injection after TBI restores microvascular flow (MVS/CAP ratio) and reduces hypoxia as reflected by NADH in a rat brain with high intracranial pressure. Mean±SEM, n=6, P<0.05.

DRPs improved neurologic outcome. At 24 hours after pMCAO, neurologic status was evaluated by a neurological scoring described by Fujii et al 1992 and in our publication [40, 41]. The average score was 2.8 for saline (n=5) and 1.9 for DRPs treated rats (n=5) showing preserved neurobehavioral function with DRP. Coordination and motor function was tested at one week after pMCAO by rotarod test. Saline animals showed a dramatic decrease in motor function reflected by a 52.7±16.1% reduction in latency compared to normal rats (FIG. 19, n=5). DRPs showed better recovery with a latency reduction by 24.4±15.7% compared to normal rats (FIG. 19, n=5).

DRPs Restored Capillary Flow, Reduced Microvascular Shunt (MVS) Flow and Attenuated Hypoxia in Hypertensive Brain.

We showed that increased intracranial pressure (ICP), also known as intracranial hypertension, compromised capillary flow and increased MVS flow (FIG. 20 A, B, D), associated with tissue hypoxia, brain edema and blood brain barrier opening; characteristic of non-nutritive MVS flow [42]. DRPs partially restored capillary flow and ameliorated MVS flow (FIG. 20 C, D) which reduced tissue hypoxia as reflected by a decrease in NADH (FIG. 20 C, D, 158±28.6% vs. 121±17.4% after DRP, Mean±SEM, n=6, P<0.05).

Fluid Percussion Injury (FPI) Model of TBI Evaluation.

Figure 21A:
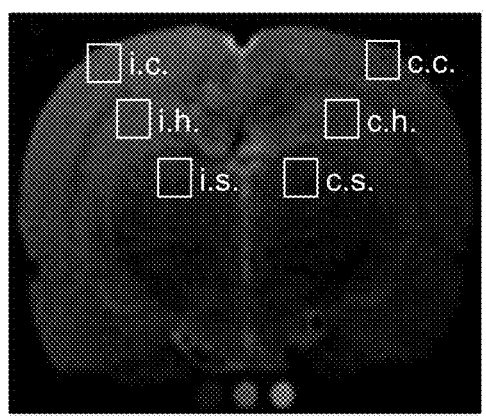
FIGS. 21A and 21B show a fluid percussion injury model of traumatic brain injury (TBI).
Figure 21B:
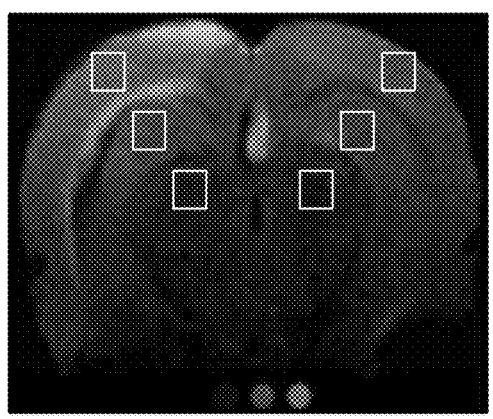
Figure 22:
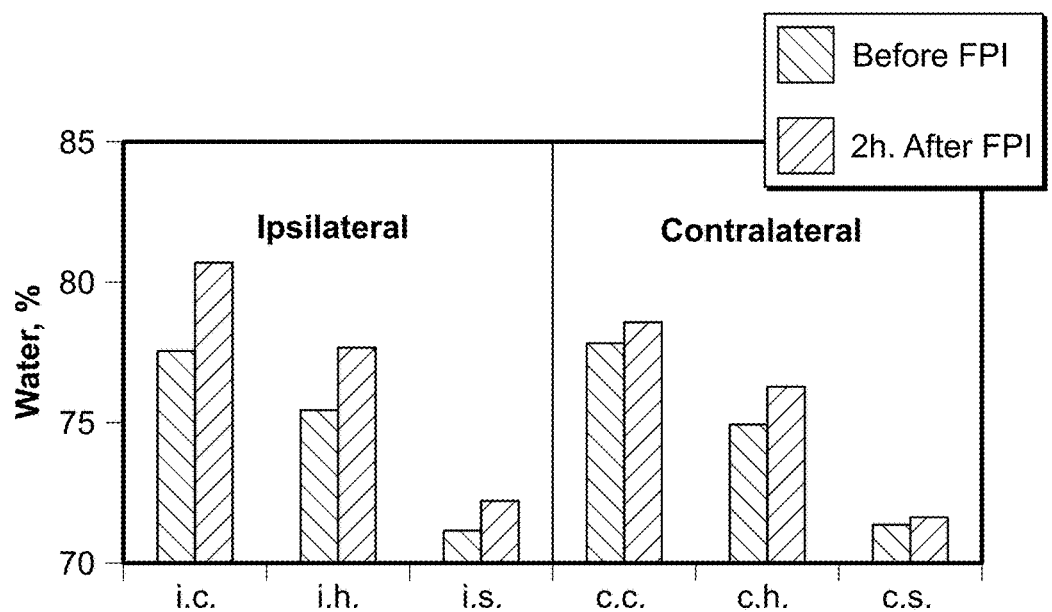
FIG. 22 is a bar graph reflecting brain edema. Calibration samples allowed for quantifying increased water content in the injured cortex and hippocampus.

We developed a TBI model resulting in sustained ICP increase by FPI transmitted onto the dura on the parietal cortex by a custom made gas driven device and tested FPI of different intensity [43, 44]. We chose a FPI of 1.5 ATA/50 ms which caused a sustained increase in ICP of 30.8±4.7 mmHg without massive subdural hemorrhage and did not alter arterial pressure (averages over 4 hours, N=10). T1 MRI (FIGS. 21A, B) revealed tissue damage in the left hemisphere after FPI (FIG. 21 B). Glass tubes (below each brain) contain calibration solutions (50, 75 and 85% of water in D2O) for quantification of water content which increased in the injured cortex from 77.6±0.35 to 80.7±0.41% and in hippocampus, from 75.4±0.38 to 77.6±0.36% 2 hours after FPI (FIG. 22).

DRPs Injection Restores Blood Flow in Collapsed Capillaries, Reduces Non-Nutritive MVS Flow, Tissue Hypoxia and BBB Damage Progression after TBI.

Figure 23:
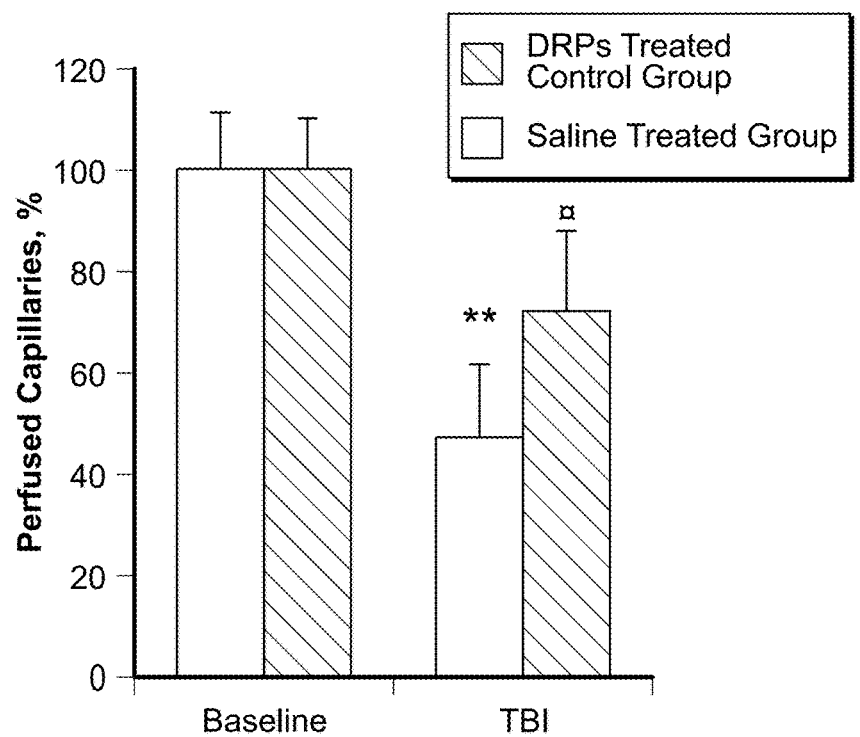
FIG. 23 is a bar graph showing that post-traumatic increase of microvascular (MVS) flow was less in the DRP treated group than in the saline-control as reflected by MVS/capillary (CAP) ratio.
Figure 24:
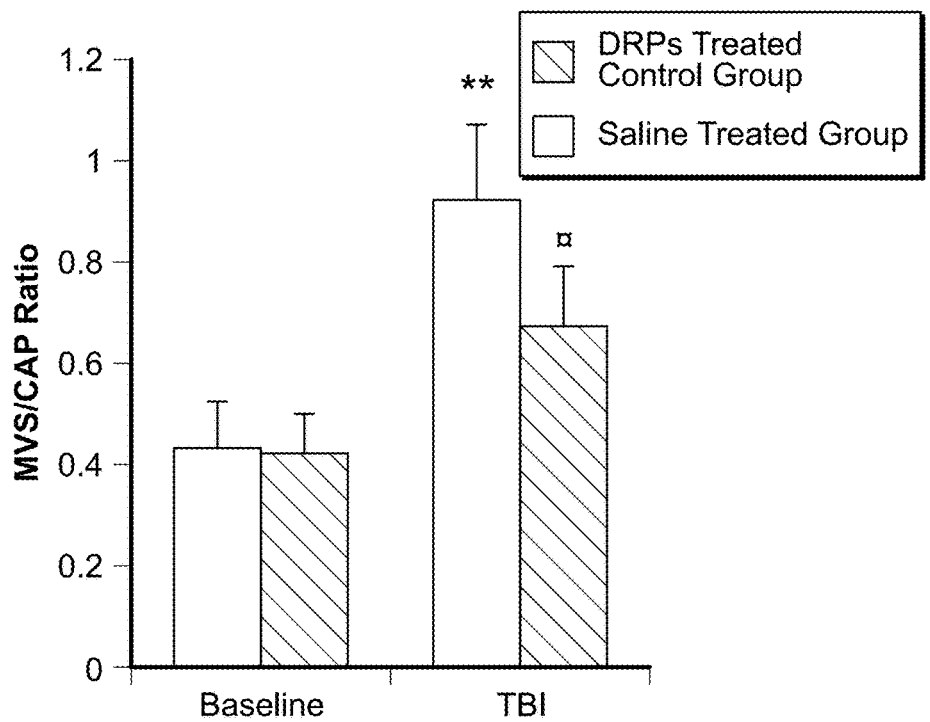
FIG. 24 is a bar graph showing that after TBI fewer capillaries were collapsed in the DRP treated group than in the saline-control group.
Figure 25:
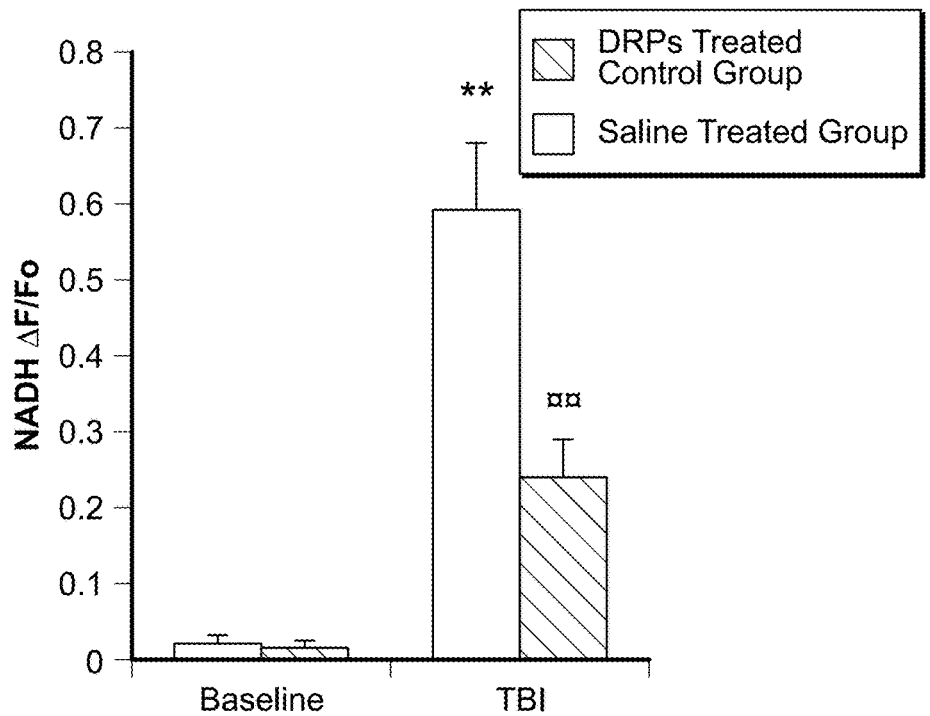
FIG. 25 is a bar graph showing that DRP treated animals showed less cortical tissue hypoxia than saline—control animals as reflected by NADH autofluorescence. Data a presented as ΔF/Fo, where Fo is pre-TBI baseline.
Figure 26:
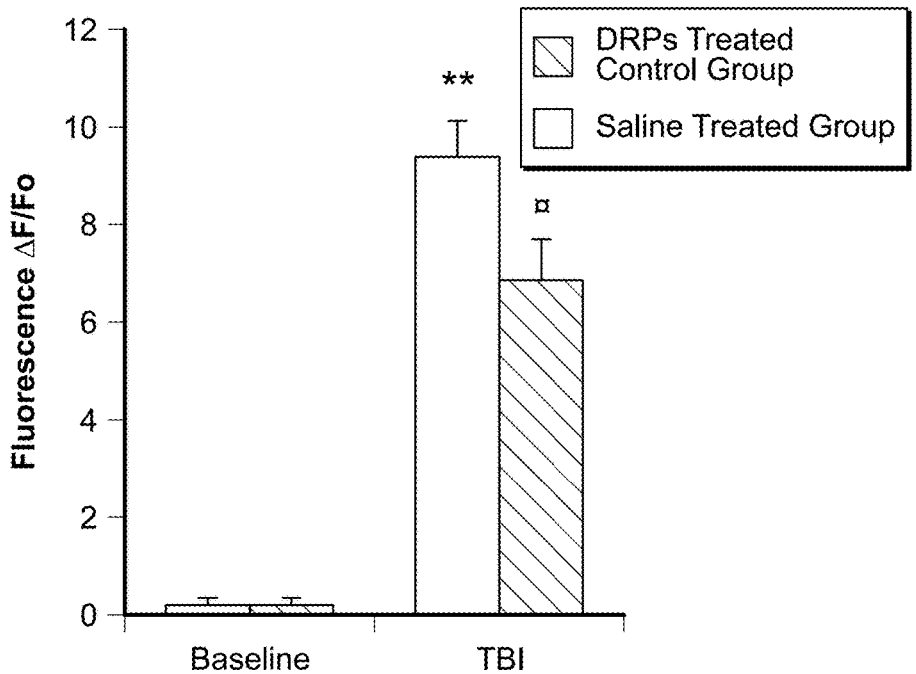
FIG. 26 is a bar graph showing that DRP treated animals had less blood brain barrier damage than saline—control animals as reflected by less cortical tissue fluorescence due to less dye extravasation. Data a presented as ΔF/Fo, where Fo is pre-TBI baseline. All data are presented as Mean±SEM, n=5 per group, ** P<0.01 compared to baseline ICP of 10 mmHg, ¤ P<0.05 compared to ICP of 40 mmHg.

We showed that TBI compromised capillary perfusion. In peri-contusion area of a saline treated brain the percent of perfused capillaries decreased to 47.3±14.4% compared to a baseline (FIG. 23, P<0.01). In DRPs treated brain, the amount of capillaries with collapsed perfusion was reduced to only 72.1±15.84% compared to a baseline (FIG. 24, P<0.05). This was significantly less than in control saline treated group (P<0.05). Fluid percussion injury in the saline treated group resulted in a sustained increase in intracranial pressure to 30.8±4.7 mmHg from the pre-injury level of 10.3±3.6 mmHg (n=5, P<0.01). In DRP treated group, the ICP raised only to 26.9±6.5 mmHg from the pre-injury level 10.5±4.1 mmHg (n=5, P<0.05), however the difference between saline and DRP treated groups was not statistically significant (P=0.18). In a control group, the rise in ICP was associated with an increase in the MVS/CAP ratio from 0.43±0.09 before injury to 1.39±0.23 after injury, respectively (FIG. 6 b, P<0.01). In DRP treated group, the MVS/CAP increased from 0.42±0.08 before injury to 0.85±0.25 after injury (P<0.05), and was significantly lower than in control group (FIG. 6 b, P<0.05). Therefore, DRP attenuated pathological MVS flow and enhanced capillary flow. Posttraumatic microvascular flow impairment in saline treated group led to tissue hypoxia, reflected by NADH accumulation (ΔF/Fo[pre-injury]=0.59±0.09, FIG. 6 c, P<0.01) compared to a baseline. Improved microvascular flow in DRP treated group mitigated tissue hypoxia; NADH autofluorescence increased only to 0.24±0.05 (FIG. 25, P<0.05 compared to a baseline and P<0.05 compared to saline treated group). TBI caused progressive damage of blood brain barrier, reflected by extravasation of fluorescent dye dissolved in a blood plasma into the tissue through vessels walls and increase tissue fluorescence which not fluorescent in an intact brain. (ΔF/Fo[pre-injury]=9.37±0.74, FIG. 26, P<0.01, compared to a baseline). In the DRP treated group BBB damage was mitigated, tissue fluorescence increased only to 6.85±0.86 (FIG. 26, P<0.05 compared to a baseline and P<0.05 compared to saline treated group).

The Long-Term Effects of DRPs on Neurologic Outcome in Rats after Traumatic Brain Injury (TBI).

Figure 27:
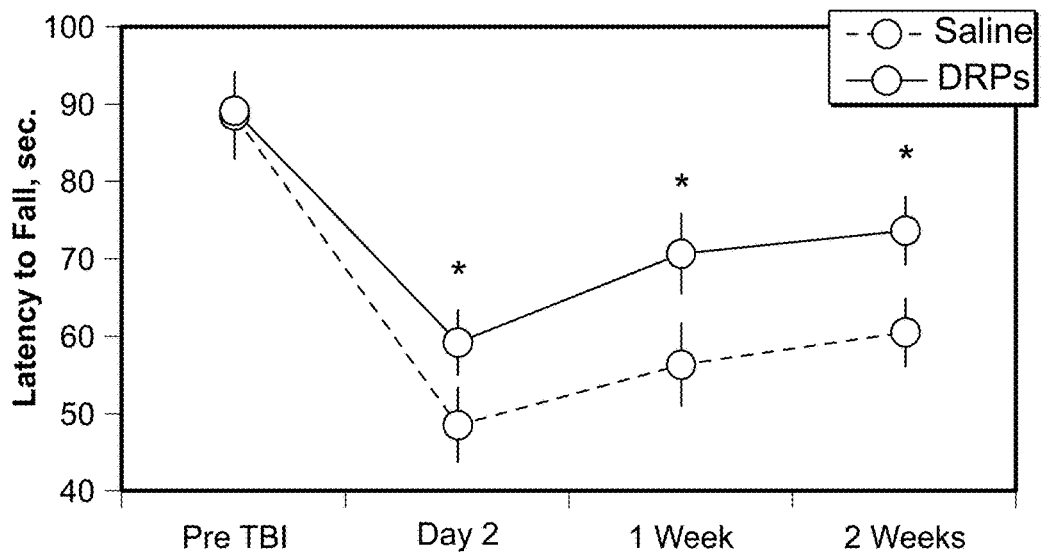
FIG. 27 is a graph showing a rotarod test for coordination and motor deficits showing better performance in DRP treated animals (n=5) than in saline treated (n=5) at 2 days after TBI and better progressive recovery for up to 2 weeks after TBI. Mean±SEM, P<0.01.

Coordination and motor deficits were tested at 2 days and 1 and 2 weeks after TBI by Rotarod test. Both, saline-control and DRPs treated animals showed a decrease in motor function, reflected by reduction in latency on a rod, compared to normal rats with gradual recovering to the $2^{nd}$ and $3^{rd}$ weeks (FIG. 27, n=5). DRPs treated animals showed better performance at $2^{nd}$ day and better progressive recovery for up to 2 weeks after TBI. Mean±SEM, P<0.01.

What is claimed is:

1. A method for treating, ameliorating or preventing acute and chronic brain ischemia comprising delivering to a subject a dosage of a drag reducing polymer (DRP) wherein the DRP is a linear, blood soluble non-toxic macromolecule with a molecular weight over 106 Daltons.

2. The method of claim 1 wherein the dosage of drag reducing polymer produces a concentration of DRP in the subject's blood of between 0.1 and 5 ppm.

3. The method of claim 1 wherein the ischemia is chronic.

4. The method of claim 3 wherein the subject is diagnosed as suffering from Alzheimer's, Parkinson's, or other types of vascular dementia.

5. The method of claim 3 wherein multiple dosages are delivered to the subject in order to maintain the concentration of DRP in the subject's blood between 0.1 and 5 ppm for an extended period of time.

6. The method of claim 5 wherein the extended period of time is longer than one week.

7. The method of claim 5 wherein the extended period of time is longer than one month.

8. The method of claim 1 further comprising measuring the blood flow of the subject's blood.

9. The method of claim 8 wherein the dosage produces an improvement in blood flow compared to the blood flow prior to treatment.

10. The method of claim 9 wherein multiple dosages are delivered to the subject in order to maintain the improved blood flow.

11. The method of claim 1 wherein the DRP is polyethylene oxide.

12. The method of claim 1 wherein the subject is at risk for an ischemic event, but is not suffering from an ischemic event at the time of delivery.

13. The method of claim 12 further comprising delivering multiple dosages to maintain a concentration of DRP in the subject's blood of between 0.5 and 5 ppm for an extended period of time.

14. The method of claim 1 wherein the subject has suffered from a stroke and is no longer eligible for tPA treatment.

15. The method of claim 1 wherein the ischemia is acute.

* * * * *